US008357426B2

(12) United States Patent
Seeney et al.

(10) Patent No.: US 8,357,426 B2
(45) Date of Patent: Jan. 22, 2013

(54) SINGLE STEP MILLING AND SURFACE COATING PROCESS FOR PREPARING STABLE NANODISPERSIONS

(75) Inventors: Charles E. Seeney, Edmond, OK (US); William A. Yuill, Edmond, OK (US); Donald D. Gibson, Edmond, OK (US)

(73) Assignee: Nanomateriales S.A. de C.V., San Pedro Garza Garcia (MX)

( * ) Notice: Subject to any disclaimer, the term of this patent is extended or adjusted under 35 U.S.C. 154(b) by 795 days.

(21) Appl. No.: 12/267,400

(22) Filed: Nov. 7, 2008

(65) Prior Publication Data

US 2009/0180976 A1 Jul. 16, 2009

Related U.S. Application Data

(60) Provisional application No. 61/020,603, filed on Jan. 11, 2008.

(51) Int. Cl.
*B05D 7/00* (2006.01)
*C09C 1/36* (2006.01)
*A61K 9/16* (2006.01)
*A61K 33/00* (2006.01)
*A61K 9/14* (2006.01)

(52) U.S. Cl. ........ 427/212; 106/436; 106/437; 424/489; 424/490; 424/600

(58) Field of Classification Search .................. 427/212; 106/436, 447; 424/489, 490, 600
See application file for complete search history.

(56) References Cited

U.S. PATENT DOCUMENTS

| | | | |
|---|---|---|---|
| 4,052,224 A | 10/1977 | Howard | |
| 4,075,031 A | 2/1978 | Allen | |
| 4,661,439 A | 4/1987 | Ruskin | |
| 5,033,682 A | 7/1991 | Braun | |
| 5,068,056 A * | 11/1991 | Robb | ............................. 516/90 |
| 5,478,675 A * | 12/1995 | Nagaura | ....................... 429/224 |
| 5,501,732 A * | 3/1996 | Niedenzu et al. | ............. 106/447 |
| 5,554,216 A | 9/1996 | Baidins et al. | |
| 5,700,318 A | 12/1997 | Brand et al. | |
| 5,707,437 A * | 1/1998 | Niedenzu et al. | ............. 106/446 |
| 5,716,751 A | 2/1998 | Bertrand et al. | |
| 5,886,069 A | 3/1999 | Bolt | |
| 5,976,237 A | 11/1999 | Halko et al. | |
| 6,086,668 A | 7/2000 | Farneth et al. | |
| 6,132,801 A | 10/2000 | Linford | |
| 6,464,965 B1 | 10/2002 | Chiarelli et al. | |
| 6,548,264 B1 | 4/2003 | Tan et al. | |
| 6,740,312 B2 | 5/2004 | Chopin et al. | |
| 6,869,596 B1 | 3/2005 | Knowland et al. | |
| 6,994,837 B2 | 2/2006 | Boulos et al. | |
| 7,152,819 B2 | 12/2006 | Ford et al. | |
| 7,264,672 B1 | 9/2007 | Trabzuni et al. | |
| 2002/0003179 A1 * | 1/2002 | Verhoff et al. | ................... 241/21 |
| 2002/0096088 A1 * | 7/2002 | Bardman et al. | .............. 106/436 |

FOREIGN PATENT DOCUMENTS

| | | |
|---|---|---|
| EP | 0 523 294 A1 | 1/1993 |
| WO | WO 89/12505 | 12/1989 |
| WO | WO 2007/100918 A3 | 9/2007 |

OTHER PUBLICATIONS

DeCastro et al., "Nanoparticles from Mechanical Attrition", *Advances in Nanophase Materials and Nanotechnology*, M.I. Barton, editor, American Scientific Publishers (2002); pp. 1-15.

Egerton et al., "The surface characterisation of coated titanium dioxide by FTIR spectroscopy of adsorbed nitrogen", *Journal of Materials Chemistry*, vol. 12, (2002-no month) pp. 1111-1117.

LMZ ZETA™ II System, NETZSCH Media mills, wet grinding, Condux, dry grinding, NETZSCH "Grinding and Dispersing Nanoparticles" edited by Henry W. Way, NETZSCH Fine Particle Technology, Exton, PA, Jun. 8, 2005.

Rayleigh scattering at Hyperphysics (http://en.wikipedia.org/wiki/Rayleigh_scattering); printed on Sep. 26, 2008; 4 pgs.

Shao et al., "Effect of Particle Size on Performance of Physical Sunscreen Formulas", (Presentation at PCIA conference—Shanghai, Cina R.P. (1999-no month); pp. 1-9.

Thiele et al., "Light-Scattering Properties of Representative, Morphological Rutile Titania Particles Studied Using a Finite-Element Method", *Journal of the American Ceramic Society*, vol. 81, No. 3, (May 1997), pp. 469-479.

\* cited by examiner

*Primary Examiner* — Abigail Fisher
(74) *Attorney, Agent, or Firm* — Dunlap Codding, P.C.

(57) ABSTRACT

A single step milling and surface coating process allows for production of a stable dispersion of surface coated nanoparticles in an efficient manner. The process comprises providing feed particles, providing a coating agent, and generating the stable dispersion of surface coated nanoparticles by milling the feed particles in an aqueous medium containing the coating agent such that the coating agent bonds to surfaces of the feed particles as the feed particles are milled to an average particle size of less than about 100 nm.

54 Claims, 2 Drawing Sheets

SINGLE STEP MILLING AND SURFACE COATING PROCESS FOR PREPARING STABLE NANODISPERSIONS

CROSS REFERENCE TO RELATED APPLICATIONS

This application claims priority of U.S. Provisional Patent Application Ser. No. 61/020,603 filed Jan. 11, 2008.

STATEMENT REGARDING FEDERALLY SPONSORED RESEARCH OR DEVELOPMENT

Not applicable.

BACKGROUND

1. Field of Invention

The present invention relates generally to improved methods for producing stable dispersions of nanoparticles and, more particularly, but not by way of limitation, to a single step milling and surface coating process for producing a stable dispersion of surface coated metal oxide nanoparticles.

2. Background of the Invention

Inorganic oxides such as titanium oxide and zinc oxide are often incorporated in cosmetics, paint, and plastics as whiteners, opacifiers, tinting agents, and the like. Particles of titanium dioxide, zinc oxide, and the like can also be used as an anti-UV agent in numerous applications, particularly in cosmetics, paint and plastics.

When used as a pigment, the performance of the particles involves absorption, reflection and scattering of visible light, which depends in large part on the particle size. For opacification, the optimum particle size of titanium dioxide is about 250 nm. When particles of titanium dioxide, zinc oxide, and the like are used as anti-UV agents, the performance involves absorption, reflection and scattering of the harmful UV radiation, and again depends to a large extent on the particle size. For example, titanium dioxide absorbs light with a wavelength of 405 nm or shorter. However, titanium dioxide also has a very high refractive index and is thus very effective in scattering. There is evidence that submicron titanium dioxide attenuates UVB (with a wavelength of from 290 to 320 nm) predominantly by absorption, while UVA (with a wavelength of from 320 to 400 nm) is attenuated predominantly by scattering.

There is a need for particle dispersions which are completely transparent, free from whitening when applied on the skin, but which still possess UV screening capabilities. It is known that when particles are smaller than one-half the wavelength of visible light, the particles will appear to form a transparent solution when completely dispersed. Thus, as anti-UV agents, the particles of titanium dioxide, zinc oxide, and the like desirably comprise a stable dispersion of nanoparticles. Nanoparticles generally refer to particles having at least one dimension of about 100 nanometers or less. Nanoparticles, unlike pigment size particles, scatter UVB light and UVA light more than the longer, visible wavelengths, and can thus prevent sunburn while remaining transparent on the skin. However, prior art processes for producing the nanoparticles are typically quite expensive and the dispersions produced are not stable.

For example, pigment particles are produced in a high-temperature reactor and then surface treated with metal silicates, dried, and further micronized to reduce particle agglomeration. Similar processes are available for producing nanoparticles which can potentially offer the desired transparency. For instance, the synthesis of nanoparticles of metals and mixed metal oxides through high-temperature oxidation of reactive precursors in oxygen plasma has been known for some time. However, plasma processing leads to agglomeration of the nanoparticles, which detracts from their desirability, especially where nanoparticle performance is required. Additionally, the high costs associated with plasma processing leads to costly end products and further limits their commercial attractiveness.

Ultra fine grinding techniques have also been investigated. As the particles become very small, their total surface area and surface energy become quite large, resulting in very high stress requirements for further fracture of the particles. Traditionally, as the particles decrease in size, the particles begin to flocculate or coagulate in order to decrease the total surface energy. Eventually particle size reduction approaches a limit and maximum energy is expended. Thus there is a need for lower cost, lower energy processes for producing metal oxide nanoparticles without aggregation and agglomeration.

Because titanium dioxide and zinc oxide are photoactive, i.e., free radical generators, to be effective in ultraviolet (UV) attenuation applications it is desirable to surface treat the titanium dioxide and zinc oxide nanoparticles to minimize or eliminate such activity. Particle absorption of a photon can result in production of a hole and an electron which can migrate to the surface of the particle and, in aqueous environments, form superoxide and hydroxyl radicals. It is known that a coating can capture these radicals and thereby reduce the apparent photoactivity.

Known processes for producing coated titanium dioxide particles typically include wet processing of particles that have been formed by plasma processing, ultrafine grinding or precipitation. During wet processing the particles are filtered, an aqueous slurry of the titanium dioxide particles is prepared, and the slurry is then treated with a metal precursor or salt to precipitate a metal oxide or hydroxide on the particle surfaces. Generally these surface coatings tend to cause additional agglomeration of the particles such that the coated titania must again be filtered, dried, re-ground to reduce agglomeration, and then redispersed. Although these coating methods can be used, the methods involve multiple energy-intensive steps.

Thus there are continuing needs for improved processes for making and coating metal oxide nanoparticles and producing stable dispersions therefrom.

SUMMARY OF THE INVENTION

One embodiment of the present invention is directed to a single step milling and surface coating process that allows for production of a stable dispersion of surface coated nanoparticles in an efficient manner. The process comprises providing feed particles, providing a coating agent, and generating the stable dispersion of surface coated nanoparticles by milling the feed particles in an aqueous medium containing the coating agent such that the coating agent bonds to surfaces of the feed particles as the feed particles are milled to an average particle size of less than about 100 nm.

In another embodiment, a method for generating a stable dispersion of surface coated nanoparticles is provided utilizing the following procedure. An aqueous slurry of feed particles, coating agent and dispersant are mixed in predetermined quantities using a disperser capable of providing shear sufficient to minimize or eliminate flocculation of the particles. The aqueous slurry is fed to an agitated media mill in closed loop with the disperser such that at least a portion of the coating agent bonds to surfaces of the feed particles as the feed particles are milled. The milled aqueous slurry from the agitated media mill is recirculated back to the disperser until the feed particles have been milled to an average particle size of less than about 100 nm.

In yet another embodiment, a process for producing a stable dispersion of nanoparticles includes first combining feed particles with a coating agent in a disperser to provide a slurry having a solids content less than about 35% by weight of slurry. The slurry is circulated to an agitated media mill in closed loop with the disperser such that at least a portion of the coating agent bonds to surfaces of the feed particles as the feed particles are milled. An additional amount of feed particles are then added to the slurry, the additional amount being sufficient to increase the solids content of the slurry to a range of from about 35% to about 75% by weight of slurry. The slurry having a solids content in the range of from about 35% to about 75% by weight of slurry is circulated to the agitated media mill in closed loop with the high-shear disperser such that the coating agent bonds to surfaces of the feed particles as the feed particles are milled to an average particle size of less than about 100 nm.

A stable dispersion of coated nanoparticles is provided which consists essentially of titanium dioxide coated with a coating material. The type and amount of coating material is capable of improving the photostability of the titanium dioxide nanoparticles. The coated nanoparticles exhibit a specific surface area greater than 150 $m^2/cm^3$ as measured by dynamic light scattering methods, and the dispersion remains stable for extended periods greater than two weeks and typically greater than several months.

Also, a stable dispersion of titanium dioxide nanoparticles having improved photostability is provided having a continuous aqueous phase with about 5 to 15 wt % citric acid and sufficient aminomethyl propanol to adjust the pH to 9.0 or higher. The dispersed phase includes anatase titanium dioxide nanoparticles having a specific surface area of at least 150 $m^2/cm^3$ as measured by dynamic light scattering. The nanoparticles are coated with a polyacrylate polymer in an amount sufficient to significantly improve the photostability of the anatase titanium dioxide nanoparticles. The coated nanoparticles are dispersed in the continuous phase.

A method for reducing the effects of ultraviolet radiation is also provided. A single step process is used to produce a stable dispersion of surface coated nanoparticles. The single step process comprises providing titanium dioxide feed particles, providing a coating agent, and generating a stable dispersion of surface coated titanium dioxide nanoparticles by milling the feed particles in an aqueous medium containing the coating agent such that the coating agent bonds to surfaces of the feed particles as the feed particles are milled to an average particle size of less than about 100 nm. The coating material is of a type, and present on the surface of the coated nanoparticles in an amount, capable of improving the photostability of the titanium dioxide nanoparticles. The stable dispersion thus produced is added to a cosmetic formulation and the cosmetic formulation is applied to a person in need of reducing the effects of ultraviolet radiation.

Thus, utilizing (1) the technology known in the art; (2) the above-referenced general description of the presently claimed and/or disclosed inventive process(es), methodology(ies), apparatus(es) and composition(s); and (3) the detailed description of the invention that follows, the advantages and novelties of the presently claimed and/or disclosed inventive process(es), methodology(ies), apparatus(es) and composition(s) would be readily apparent to one of ordinary skill in the art.

DETAILED DESCRIPTION OF THE INVENTION

Figure 1:
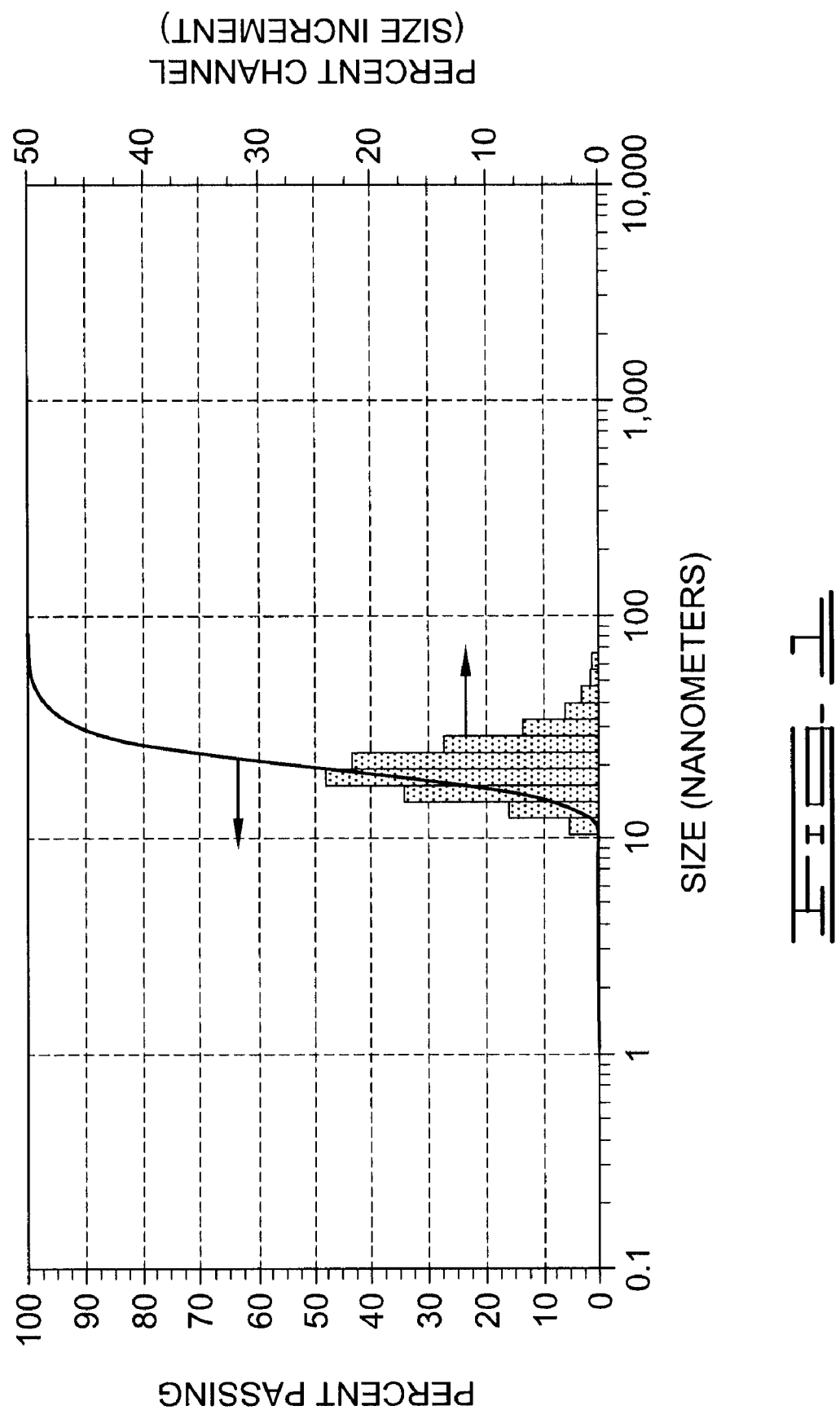
FIG. 1 is a graphical representation of the particle size distribution of a nanodispersion produced using the procedure described in Example 2 of the present disclosure.

Before explaining at least one embodiment of the invention in detail, it is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

As mentioned above, many applications for metal oxides require stable dispersions of nanosize coated metal oxide particles. The present invention provides a single step milling and surface coating process for producing a stable dispersion of surface coated nanoparticles, thus avoiding the multiple energy intensive steps used in much of the prior art. Feed particles and a coating agent are milled together in an aqueous medium such that the coating agent bonds to surfaces of the feed particles as the feed particles are milled to nanoparticles. The term "nanoparticles" as used herein refers to particles having at least one dimension of about 100 nanometers or less.

Any metal oxide feed particle can be used. Suitable feed particles for UV-screening applications include, but are not limited to, titanium dioxide, zinc oxide, zinc titanate and iron oxide. In one embodiment, the feed particles comprise titanium dioxide. In another embodiment, the feed particles comprise a mixture of titanium dioxide and zinc oxide. Feed particles generally have an average particle size in a range of from about 100 nm to about 2500 nm prior to milling. For example, feed particles comprising metal oxides, such as titanium and zinc oxides, are generally pigment grade or agglomerated forms where the particle size range can extend from 150 nm to 1500 nm and greater.

Titanium dioxide feed particles can be either anatase or rutile, both of which are readily available commercially as, for example, pigments. Anatase is produced by a process commonly known as the sulfate process. Illmenite is dissolved in sulfuric acid and the by-product iron sulfate is crystallized out of solution. The dissolved titanium is further purified and precipitated to yield anatase titanium dioxide particles.

Rutile is produced using the chloride process wherein crude titanium dioxide is purified via titanium tetrachloride. The ore or enriched ore is carbochlorinated with carbon and chlorine to give a titanium tetrachloride vapor. This titanium tetrachloride is purified and re-oxidized with oxygen to give predominantly rutile titanium dioxide.

Preferably, the titanium dioxide crystal structure is predominantly anatase; however, a rutile titanium dioxide crystal structure and mixtures of anatase and rutile can also be used. In certain applications, such as cosmetics and dermal care products, the rutile form (a hard crystal) is less desirable than the anatase form (a softer crystal). When pigment is used as the feed material, the feed particles typically have an average primary particle size of about 0.2 micron (200 nm) or greater to optimize the light scattering capability of the pigment particles and are typically agglomerated to form much larger agglomerates.

Zinc oxide is a base white pigment used in paints, cosmetics, and as an opaque sunscreen. It is also used in the rubber industry, electronic materials and medical applications. Zinc oxide can be manufactured by gas phase chemical deposition, spray pyrolysis and sol gel methods. The French process for manufacture of zinc oxide involves melting metallic zinc in a graphite crucible and vaporizing the zinc metal at high temperatures. The zinc vapor reacts with oxygen to produce zinc oxide particles which are cooled and collected in a bag house.

In one embodiment of the present invention, the feed particles comprise a mixture of anatase and zinc oxide. Milling mixtures of anatase and zinc oxide appears to have a synergistic effect on the photocatalytic properties of the particles. Surprisingly, and as described in more detail hereinafter, a mixture of anatase and zinc oxide milled and coated together according to an embodiment of this invention, results in a reduced photocatalytic activity compared to a mixture having the same chemical composition but not milled and coated together. When titanium dioxide and zinc oxide are milled together, the weight ratio of titanium dioxide to zinc oxide is preferably in a range of from about 1:10 to about 10:1, and more preferably in a range of from about 2:1 to about 1:2.

An aqueous medium and the feed particles to be milled are first combined, preferably in a disperser or high-shear mixer, to form a slurry. The terms "disperser" and "high-shear mixer" are used interchangeably herein and mixing time can extend up to three to four hours. The aqueous medium comprises water, wherein the term "water" is used includes groundwater, sea water, and brines as well as treated water such as deionized or distilled water. Preferably, the water is deionized or distilled. Feed particles are typically added to the aqueous medium to form a slurry having a wt % solids in the range of from about 10 to about 40 wt %, and preferably in the range of from about 25 to about 30 wt %. The slurry pH is monitored and adjusted with, for example, aminomethyl propanol (AMP-95™) to maintain a minimum basic pH level of about 9.0. Additional feed particles can be added to increase the total solids content to a range of from about 50% to about 70 wt %.

As discussed previously, oxides such as titanium dioxide and zinc oxide can provide excellent UV protection; however, a disadvantage is their photocatalytic activity. By generating free radicals, the particles can accelerate degradation of constituents in the carrier composition. Photocatalytic activity is reduced by covering the particle surfaces with a coating or coating agents. Prior art coating procedures involve adding coating agents to the particles in a separate step after the particles have been reduced to the desired size. Aggregation due to the coating process is then reduced by milling the coated aggregates in yet another separate step. However, it has presently been discovered that the particle surfaces can be coated while the particles are being milled such that the coating agent binds to the surface of the feed particles and to the newly formed surfaces of the feed particles during milling to provide a surface coating on the nanoparticles. It has been found that such a single step milling and coating process synergistically improves coating efficiency and coated particle properties.

Coating agents can be organic as well as inorganic compounds, or a combination of both, wherein the compounds are capable of bonding to the surface of the oxide particle. Examples of suitable organic compounds include, but are not limited to acrylate polymers, organosilicon copolymers and organosilicon compounds. Preferably, a polyacrylate polymer such as ammonium polyacrylate is used. Ammonium polyacrylate is available commercially as, for example, Darvan® from R.T. Vanderbilt Company, Inc. of Norwalk, Conn. This results in an organic surface treatment that incorporates new performance properties in the final nanodispersion. The optimum amount of organic coating agent varies, but is typically in a range of from about 5% to about 25% of the total feed particle weight. Preferably the amount of organic coating agent added is in a range of from about 5% to about 10% of the total feed particle weight. The coating can be added to the disperser or directly to the mill.

Many inorganic coating agents can be utilized. For example, soluble metal compounds can be added such that at least one metal oxide, hydroxide, or hydrated oxide binds to the surface of the feed particles and to the newly formed surfaces of the feed particles during milling to provide a surface coating on the surface coated nanoparticles. Suitable metal compounds include, but are not limited to, soluble salts, oxides and hydroxides of aluminum, zinc, calcium, tin, iron and zirconium. In one embodiment, the soluble metal compound may preferably be sodium aluminate. A silicate such as sodium silicate or silicic acid, and metal silicates such as aluminum silicate may also be used as coating agents. In this case the silicate binds to the surfaces of the feed particles as the feed particles are milled to nanoparticles.

The amount of inorganic coating agent varies but is typically in a range of from about 0.5% to about 20% of the total feed particle weight. Preferably, the amount of inorganic coating agent added is in a range of from about 0.5% to about 5% of the total feed particle weight.

Because the coating process occurs while milling, insoluble coating compounds can be added such that the surfaces of the coating compound can adhere to or react with the surfaces of the feed particles during compaction. For example, milling a mixture of zinc oxide and titanium dioxide together can produce nanoparticles with a reduced photocatalytic activity compared to a mixture having the same chemical composition but not milled and coated together. While not limiting the invention to any particular theoretical mechanism, it is believed that compaction of a titanium dioxide surface with a zinc oxide surface can result in formation of a zinc/titanium compound such as zinc titanate on the surfaces in a manner similar to mechanical alloying processes used with elemental powders.

Coating of the particles generally improves the photocatalytic activity of the particles. Photocatalytic activity is typically measured relative to a standard. For example, the sample can be suspended in a 0.40M solution of 2-propanol in pentane and irradiated with UV light for a specified time. The concentration of acetone formed is measured and compared to the acetone formed from a standard under the same conditions. Conversion of 2-propanol is determined by gas chromatography. Acetone concentration is typically used to measure photocatalytic activity because the rate of formation follows a zero order kinetics model.

Typically a dispersant such as an organic acid is added to the slurry prior to milling. The dispersant aids in the creation of a nanodispersion as the milling process proceeds and the feed particles are reduced in size. The dispersant used in this invention can be any dispersant known in the art to be useful in the fine grinding of metal oxides and includes, but is not limited to, citric acid, sodium or potassium pyrophosphate, aliphatic carboxilic acids, polyhydroxy alcohols, triethanol amine (TEA), and 2-amino 2-methyl 1-propanol (AMP™), monoisopropylamine, and mixtures thereof. A preferred organic acid dispersant is citric acid.

The amount of organic acid dispersant added can be in the range of from about 1% to about 20% based on the weight of feed particles. Preferably about 10% dispersant based on the weight of feed particles is added. It is common practice to add all of the dispersant to the slurry in the disperser at the start of milling. In some instances, however, it is advantageous to add the dispersant gradually during milling in amounts to ensure minimal flocculation of the feed particles during milling.

Good dispersion is beneficial to enable milling to the nanoparticle size range. However, long term dispersion is additionally required when the nanoparticles are used in applications such as sunscreens and cosmetics. It is known to add certain dispersing agents to coated titania particles to produce a nanoparticle suspension; however, prior art suspensions do not typically remain stable for long periods of time. In such applications, reagglomeration of the nanoparticles over time results in a "rough" feeling when spread onto the skin and general aesthetically undesirable characteristics.

Upon preparation of the desired slurry composition, the resulting feed slurry is charged to an attritor or agitated media mill to begin the size reduction process. Suitable agitated media mills are known to those skilled in the art. For example, one such suitable mill is a bead mill manufactured by and available from Netzsch, Inc. The North American subsidiary of the Netzsch operating companies is located in Exton, Pa.

The agitated media mill, sometimes referred to herein as a bead mill, is employed to shear or reduce the feed particles to the nanoscale (<100 nm) range from a large starting size that can be microns in range. The mill is charged with the appropriate amount of media, typically 70 to 95 vol %, preferably 85 to 95 vol %, and the remaining mill volume is charged with feed slurry from the disperser. Under the appropriate conditions of milling media, temperature, flow and mill rotation, the feed particles can be rapidly reduced to nanoscale size.

The milling media is comprised of dense beads of materials such as yttria stabilized zirconia in a uniform size range to achieve desired product particle size ranges. For example, a milling media composed of 100 to 200 micron zirconia will generally produce a limiting product size of approximately 100 nm. A milling media composed of 50 to 100 micron zirconia will similarly produce a limiting product size of approximately 50 nm. Preferably the milling media is zirconia having a particle size less than 200 microns. In some instances it is desirable to use zirconia milling media with a particle size in the range of from about 30 microns to about 50 microns. Of course, the milling media alone does not lead to stable nanodispersions.

The energy expended in milling causes a significant temperature increase in the mill. As understood by those skilled in the art, temperature can be controlled by a number of means, such as by utilizing cooling water with a jacketed mill or by circulating the slurries through a heat exchanger with cooling water. A heat exchanger can also be disposed within the disperser. Preferably, the temperature is maintained at 45° C. or less inside the mill to avoid damage to temperature-sensitive seals and the like.

The milling process is monitored and controlled to produce the desired surface area or particle diameter. BET surface area is understood to mean the specific surface area determined by nitrogen adsorption in accordance with ASTM standards. Particle size can also be determined by transmission electron microscopy (TEM) and by particle size distribution as determined by a particle size analyzer using dynamic light scattering. When the surface area is calculated based on the particle size distribution measured by dynamic light scattering, the specific surface area computation typically assumes smooth, solid, spherical particles as opposed to a BET or other adsorption based surface area determination.

The milling process is preferably monitored by a particle size analyzer, such as the NanoTrak available from MicroTrak Systems, Inc. of Eagle Lake, Minn. Samples from the milling volume are taken periodically and measured for volume average and number average particle diameter and specific surface area.

As the nanomaterial specific surface area increases during the run, from an initial 10 to 20 $m^2/cm^3$ (for roughly 1-5 micron diameter feed particles) to greater than 200 $m^2/cm^3$ (for roughly 30 nm diameter particles), the appearance of the slurry changes from a white dispersion, from which oxide particles will precipitate or settle, to an opaque or translucent nanodispersion, from which no particles will precipitate or settle. This transition occurs around 150 $m^2/cm^3$ or roughly 50 nm diameter particles. The process can be terminated at this point or continued to produce higher surface area materials. The coated nanosize product at this point is referred to as an intermediate and can be used as the base for preparing coating or cosmetic formulations.

In one embodiment, the feed slurry is initially subjected to dispersion, sometimes referred to herein as high-shear mixing, for a period of hours, during which the slurry pH is monitored and adjusted with, for example, aminomethyl propanol (AMP-95™) to maintain a minimum basic pH level of about 9.0. The terms "dispersion" and "high-shear mixing" are used herein and in the appended claims to mean mixing with sufficient shear to minimize particle agglomeration and particle flocculation. As understood by those skilled in the art, the actual disperser design and operation can vary with feed source, solids loading, slurry chemistry, and other operating conditions. Slurry from the disperser is fed to an agitated media mill in closed loop with the disperser such that at least a portion of the coating agent bonds to surfaces of the feed particles as the feed particles are milled. Particle agglomeration and flocculation are minimized by alternating high shear mixing with high shear milling. The slurry is recirculated until the feed particles are milled to an average particle size of less than about 100 nm.

In another embodiment, feed particles are dispersed and combined with a coating agent in a disperser to provide a slurry having a solids content less than about 35% by weight of slurry. The slurry is circulated to an agitated media mill in closed loop with the disperser such that at least a portion of the coating agent bonds to surfaces of the feed particles as the feed particles are milled. After milling for a time, an additional amount of feed particles are then supplied to the slurry to bring the solids content to a range of from about 45% to about 75% by weight of slurry. Staging the addition of feed particles allows preparation of a nanoparticle dispersion with higher solids content than would otherwise be possible. Staging also allows for broadening the particle size distribution if desired for UVA and UVB attenuation.

The process technology can be further extended to the specific preparation of various finished product formulations. For example, in the preparation of cosmetic or skin care formulations, the formulation ingredients or components are added to the mill and processed using 100 micron milling media. The formulation is processed to a predetermined end point of viscosity and consistency and can be moved directly to filling stages.

In order to further illustrate the present invention, the following examples are given. However, it is to be understood that the examples are for illustrative purposes only and are not to be construed as limiting the scope of the invention.

EXAMPLE 1

In this experiment, a 0.5 L MiniCer laboratory grinding system (available commercially from Netzsch, Inc.) is used. Feed particles of commercially available anatase pigment having an average primary particle size of 0.25 micron are mixed with deionized water and reagents to form about 350 mL of slurry comprising 15 wt % anatase, 10 wt % citric acid, and 5 wt % Darvan®7-N (ammonium polyacrylate). The pH is adjusted to 9.2 with aminomethyl propanol (AMP-95™). The slurry is mixed for 5 hours in a disperser using a high shear mixer. The mill is filled with about 150 mL of YTZ® grinding media (yttrium stabilized zirconia) having a particle size of 0.05 mm. The dispersed slurry is then fed continuously through the mill and recirculated through the disperser. The disperser is water cooled to maintain a temperature between 20° C. to 30° C.

The feed particles are milled for 30 minutes after which a sample is removed and analyzed for particle size distribution using a NanoTrak™ particle size analyzer. The feed particles are milled for another 30 minutes after which another sample is removed and analyzed for particle size distribution. Milling and sampling continue for 6.5 hours. Table 1 shows the average particle size achieved at each 30 minute sampling point. As understood by those skilled in the art, the term "MV" refers to the mean diameter, in nanometers, of the volume distribution and represents the center of gravity of that distribution. The average particle size based on the volume distribution is strongly influenced by coarse particles. The term "MN" refers to the mean diameter, in nanometers, of the number distribution and is weighted to the smaller particles. The term "CS" refers to the calculated specific surface area in $m^2/cm^3$. The computation assumes smooth, solid, spherical particles as opposed to a BET or other adsorption based surface area determination.

TABLE I

Particle Size versus Milling Time

| Time (min) | MV (nm) | MN (nm) | CS ($m^2/cm^3$) |
|---|---|---|---|
| 30 | 96.2 | 65.1 | 71.99 |
| 60 | 169.9 | 82.5 | 44.2 |
| 90 | 159.9 | 75 | 46.61 |
| 120 | 128.6 | 37.6 | 56.46 |
| 150 | 107.9 | 43.6 | 72.84 |
| 180 | 59 | 29.13 | 139.6 |
| 210 | 38.4 | 25.58 | 191.3 |
| 240 | 30.8 | 23.01 | 218.1 |
| 270 | 27.73 | 21.57 | 240.1 |
| 300 | 25.12 | 19.92 | 259.8 |
| 330 | 23.54 | 18.9 | 275.5 |
| 360 | 22.78 | 17.86 | 290.3 |
| 390 | 22.63 | 17.88 | 296.8 |

EXAMPLE 2

A 10-liter bead mill from Netzch, Inc. is used to mill a commercially available anatase pigment having an average primary particle size of about 0.25 micron and an agglomerated particle size of about 1.5 micron. The pigment is mixed with deionized water and reagents to form about 60 gal of slurry comprising about 45 wt % anatase, and 5 wt % reagents. Reagents include citric acid and Darvan®7-N. The pH is adjusted to about 9 with aminomethyl propanol (AMP-95™). The slurry is dispersed for about 4 hours in an 80 gal disperser equipped with a high shear mixer. The mill is about 90 vol % charged with YTZ® grinding media having a particle size in the range of 100 to 200 micron and finer. The dispersed slurry is then fed continuously through the mill and recirculated through the disperser while maintaining the temperature at less than about 45° C. to avoid damage to synthetic materials in the mill. After 5-6 hours, surface areas exceeding 500 $m^2/cm^3$ are achieved and the resulting dispersion remains stable for at least two weeks and typically for greater than two months. FIG. 1 shows a typical product particle size distribution.

EXAMPLE 3

The procedure described in Example 2 is modified such that the slurry initially contains only a portion of the anatase feed particles and reagents in a 25% solids slurry. The initial slurry is dispersed for 1-2 hours and then circulated through the mill in closed loop with the disperser for several additional hours, after which the remaining anatase feed particles and reagents are added to the slurry. The resulting slurry contains 55% solids by weight and is circulated through the mill for several additional hours giving a total milling and dispersion time of about 5-6 hours.

Figure 2:
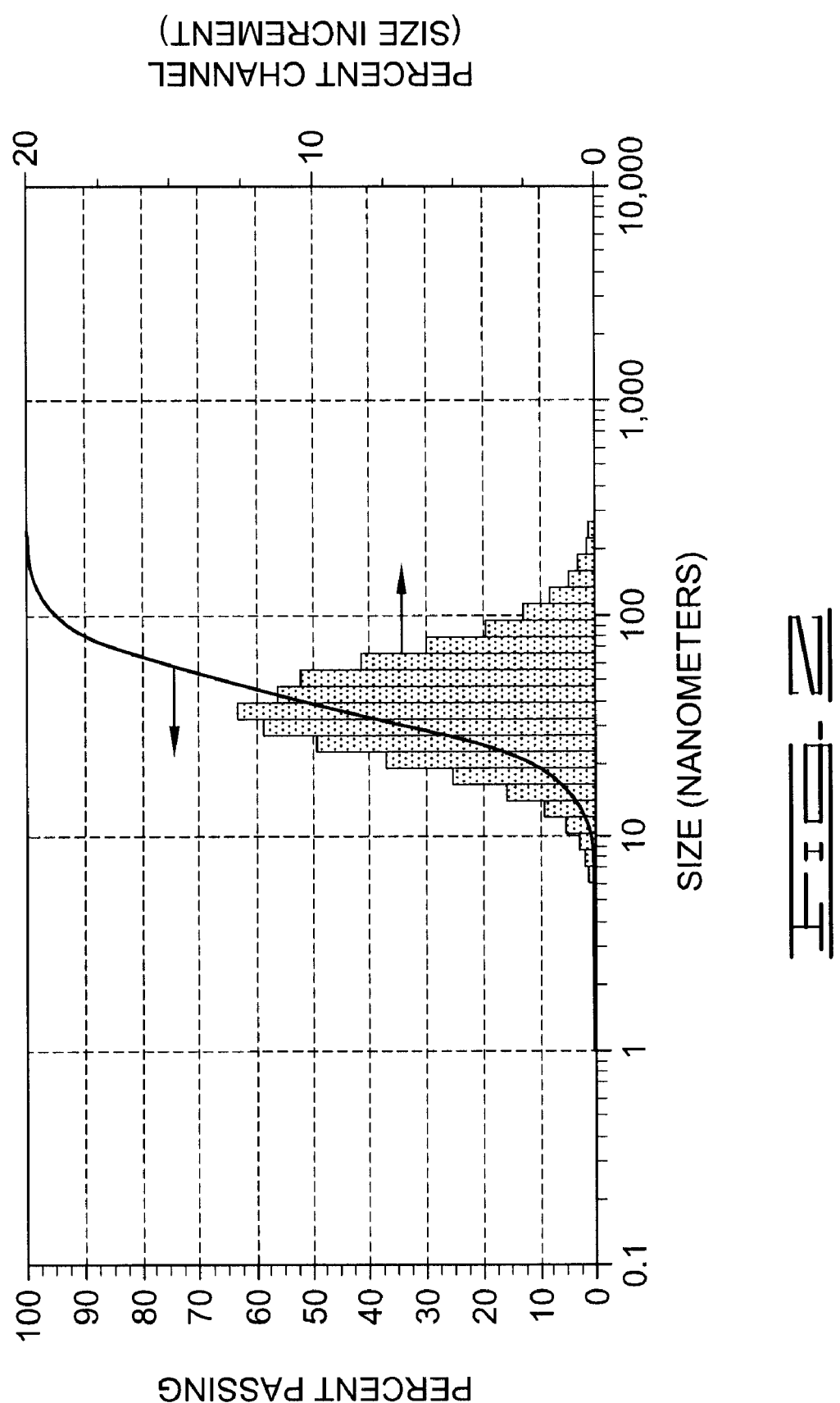
FIG. 2 is a graphical representation of the particle size distribution of a nanodispersion produced using the procedure described in Example 3 of the present disclosure.

FIG. 2 shows a product particle size distribution using the above procedure. The broad nature of the particle size distribution is more pronounced. Such a broad distribution can be very desirable for screening both UVA and UVB in sun screen formulations and applications. In addition, it is possible to produce a stable and very high solids dispersion of titania nanoparticles.

EXAMPLE 4

The photoactivity of an anatase nanodispersion having an organic coating of Darvan®7-N and produced according to Example 1 was compared to AEROXIDE® P25, a commercially available uncoated nanoparticle titania from Degussa (now Evonik Industries). Sample dispersions of the commercial grade and the product produced by this invention were placed in contact with polyethylene films and exposed to a period of UV radiation. The product produced by Example 1 of this invention exhibited no UV effects on the film while the commercial uncoated grade exhibited marks and discoloration on the film.

EXAMPLE 5

The procedures of this invention may also be used to treat zinc titanate to produce substantially stable dispersions of nanoparticles. Zinc titanate feed particles having an average agglomerated particle size of 1-5 micron are milled using a 0.5 L MiniCer laboratory grinding system. The feed particles are mixed with deionized water and reagents to form about 350 mL of premix slurry comprising 15 wt % zinc titanate, 10 wt % citric acid, and 5 wt % Darvan®7-N (ammonium polyacrylate). The pH is adjusted to 9.2 with aminomethyl propanol (AMP-95™). The slurry is mixed in the disperser while the mill is filled with about 150 mL of YTZ® grinding media having a particle size in the range of 100 to 200 micron. The dispersed slurry is then fed continuously through the mill and recirculated through the water cooled disperser while maintaining a temperature of 45° C. The zinc titanate feed particles are milled and circulated for a total of 5 hours.

EXAMPLE 6

A dispersion of silica-coated titania nanoparticles may be produced using the following procedures. Feed particles of commercially available anatase pigment having an average primary particle size of 0.25 micron are mixed with deionized water and reagents to form about 350 mL of slurry containing about 30 wt % anatase, about 5 wt % citric acid, and about 8 wt % sodium silicate. The pH is adjusted to 9.0 with either aminomethyl propanol (AMP-95™) or additional citric acid depending on the alkalinity of the sodium silicate. The slurry is dispersed for about 1 hour in a disperser using a high shear mixer. The 0.5 L MiniCer laboratory grinding system is filled with about 150 mL of YTZ® grinding media (yttrium stabilized zirconia) having an average particle size of about 50 micron. The dispersed slurry is fed continuously through the mill and recirculated through the disperser. The mill is jacketed and water cooled to maintain a temperature less than about 40° C. to avoid damage to the mill, and the temperature of the slurry in the disperser is controlled to a temperature in the range of from about 45° C. to about 60° C.

The feed particles are milled for about 3 hours while samples are removed and analyzed to determine degree of flocculation and primary particle size distribution. Darvan®7-N is added to reduce or eliminate flocculation. The pH is monitored and adjusted to provide the desired silica coating on the titania nanoparticles.

EXAMPLE 7

A dispersion of alumina-coated titania nanoparticles may be produced using the following procedures. Feed particles of commercially available anatase pigment having an average primary particle size of 0.25 micron are mixed with deionized water and reagents to form about 60 gal of slurry containing about 30 wt % anatase, about 3 wt % citric acid, and about 8 wt % sodium silicate. The pH is adjusted to 9.0 with either aminomethyl propanol (AMP-95™) or additional citric acid, depending on the alkalinity of the sodium aluminate. The slurry is dispersed for about 1 hour in a disperser using a high shear mixer. A 10-liter bead mill from Netzch, Inc. is about 90% filled with YTZ® grinding media having an average particle of about 100 micron. The dispersed slurry is then fed continuously through the mill and recirculated through the disperser. The disperser is maintained at about 60° C. to 70° C. and the mill is jacketed and water cooled to maintain the temperature less than about 45° C.

The feed particles are milled for about 3 hours while samples are removed and analyzed to determine degree of flocculation and primary particle size distribution. Darvan®7-N is added to reduce or eliminate flocculation. The pH is monitored and adjusted to provide the desired alumina coating on the titania nanoparticles.

EXAMPLE 8

Feed particles of commercially available anatase pigment having an average primary particle size of 0.22 micron are mixed with zinc oxide pigment having an average primary particle size of 0.23 micron. The pigments are combined in a 1:1 weight ratio and are mixed with deionized water and reagents to form about 350 mL of slurry comprising 15 wt % anatase and zinc oxide, 10 wt % citric acid, and 5 wt % Darvan®7-N (ammonium polyacrylate). The pH is adjusted to 9.2 with aminomethyl propanol (AMP-95™). The slurry is dispersed for 2 hours in a disperser using a high shear mixer. The mill is filled with about 150 mL of YTZ® grinding media (yttrium stabilized zirconia) having a particle size of 0.05 mm. The dispersed slurry is then fed continuously through the mill and recirculated through the disperser. Slurry in the mill and disperser is cooled to maintain a temperature of less than about 45° C.

The anatase and zinc oxide feed particles are milled and circulated through the disperser for a total of about 5 hours. The resulting dispersion of anatase and zinc oxide nanoparticles has an average primary particle size of about 30 nm. The solids content of the resulting nanodispersion can be increased from about 25-30 wt % to about 50 wt % by adding additional feed particles to the disperser after milling the lower solids content slurry for about 1 to 2 hours. The photocatalytic properties of the resulting dispersions are measured by coating a clear plastic sheet with a known weight of dispersion, pressing it down, and using a UV meter to measure the total UVA and UVB penetrating the sheet while exposed perpendicularly to sunlight. The UV penetrating is compared to the total UV exposure in the sunlight and the results are expressed as % UVA/UVB blocking efficiency. A 25% solids nanoparticle dispersion blocks about 85% to 90% of the UVA/UVB radiation while a 50% solids dispersion blocks about 95% to about 99% of the UVA/UVB radiation.

EXAMPLE 9

Sunscreen formulations: SPF measurements show that cosmetic formulations containing 1 wt % and 5 wt % nanosize titanium dioxide (>150 m$^2$/cm$^3$) provide SPF protection of 15 and 35, respectively. Dermal care formulations are also clear on application, not leaving white residues typical of larger particle sized titanium dioxide or zinc oxide.

From the above description, it is clear that the present inventive process(es), methodology(ies), apparatus(es) and composition(s) are well adapted to carry out the objects and to attain the advantages mentioned herein as well as those inherent in the presently provided disclosure. While presently preferred embodiments of the invention have been described for purposes of this disclosure, it will be understood that numerous changes may be made which will readily suggest themselves to those skilled in the art and which are accomplished within the spirit of the presently claimed and disclosed inventive process(es), methodology(ies), apparatus(es) and composition(s) described herein.

What is claimed is:

1. A single step milling and surface coating process for producing a stable dispersion of surface coated nanoparticles, the single step process comprising:
    combining feed particles comprising titanium dioxide having an anatase crystalline structure and an average primary particle size of 200 nm or greater with an aqueous medium containing a coating agent; and
    generating a stable aqueous dispersion of surface coated nanoparticles by milling the feed particles at a concentration of 10% to 40% by weight in the aqueous medium containing the coating agent such that the coating agent bonds to surfaces of the feed particles as the feed particles are milled to an average particle size of 100 nm or less.

2. The process of claim 1, wherein the feed particles have an average particle size of from about 200 nm to about 2500 nm prior to milling.

3. The process of claim 1, wherein the coating agent includes a polymer or copolymer comprising acrylates or organosilicon compounds.

4. The process of claim 1, wherein the coating agent comprises ammonium polyacrylate.

5. The process of claim 1, wherein the coating agent comprises at least one water soluble metal compound that binds to surfaces of the feed particles and to newly formed surfaces of the feed particles as a metal oxide, hydroxide or hydrous oxide to form the surface coating of the surface coated nanoparticles.

6. The process of claim 5, wherein the at least one water soluble metal compound comprises a metal selected from the group consisting of zinc, aluminum, zirconium, titanium, iron, calcium or a combination thereof.

7. The process of claim 1, wherein the coating agent comprises at least one water soluble silicate compound that binds to surfaces of the feed particles and to newly formed surfaces of the feed particles as a hydrous silicate or hydrous metal silicate to form the surface coating of the surface coated nanoparticles.

8. The process of claim 1, wherein the feed particles comprise titanium dioxide and the resulting surface coated nanoparticles have improved photostability compared to uncoated nanoparticles of the titanium dioxide.

9. The process of claim 1, wherein the aqueous medium comprises deionized or distilled water.

10. The process of claim 1, wherein the feed particles are present in the aqueous medium in an amount in the range of from about 25% to about 30% by weight.

11. The process of claim 1, wherein the aqueous medium additionally contains a dispersant.

12. The process of claim 11 wherein the dispersant comprises an organic acid and/or a salt of the organic acid.

13. The process of claim 11, wherein the dispersant is selected from the group consisting of citric acid, polyacrylates, sodium or potassium pyrophosphate, aliphatic carboxylic acids, polyhydroxy alcohols, triethanol amine, 2-amino 2-methyl 1-propanol triethanolamine, 2-amino-2-methyl-1-propanol, monoisopropylamine, and mixtures thereof.

14. The process of claim 11, wherein the dispersant comprises citric acid, a salt of citric acid, or a combination of citric acid and a salt of citric acid.

15. The process of claim 11, wherein the dispersant is present in the aqueous medium in an amount in the range of from about 1% to about 20% by weight of aqueous medium.

16. The process of claim 1, wherein the pH of the aqueous medium is monitored and adjusted.

17. The process of claim 1, wherein the pH of the aqueous medium is monitored and adjusted with aminomethyl propanol to maintain a basic pH of about 9.0 to 9.5.

18. The process of claim 1, wherein milling and coating the feed particles is achieved in an agitated media mill using a milling media comprising beads.

19. The process of claim 18, wherein the milling media comprises zirconia beads having a particle size of 200 nm or less.

20. The process of claim 18, wherein the milling media comprises zirconia beads having a particle size in the range of from about 50 micron to about 100 micron.

21. The process of claim 18, wherein the agitated media mill is filled to about 85 to 95 vol % with milling media.

22. The process of claim 18, wherein the feed particles and aqueous medium are cycled from a disperser to the agitated media mill.

23. The process of claim 22, wherein the disperser is equipped with a mixer capable of providing shear sufficient to minimize particle agglomeration and flocculation.

24. The process of claim 22, further comprising selecting a temperature and maintaining the temperature in the agitated media mill.

25. The process of claim 24, further comprising maintaining the temperature in the agitated media mill at about 45° C. or less.

26. The process of claim 24, wherein the coating agent comprises at least one water soluble metal compound that binds to surfaces of the feed particles and to newly formed surfaces of the feed particles as a metal oxide, hydroxide or hydrous oxide to form the surface coating for the surface coated nanoparticles, the process further comprising maintaining the temperature in the disperser in a range of from about 45° C. to about 85° C.

27. The process of claim 1, wherein the dispersion of surface coated nanoparticles remains in a stable dispersed state for a period greater than two months.

28. A method for generating a stable aqueous dispersion of surface coated nanoparticles, the method comprising:
mixing an aqueous slurry of 10% to 40% by weight feed particles, with coating agent and dispersant in predetermined quantities in a disperser using shear sufficient to minimize flocculation, wherein the feed particles comprise titanium dioxide having an anatase crystalline structure and an average primary particle size of 200 nm or greater;
feeding the aqueous slurry to an agitated media mill in closed loop with the disperser such that at least a portion of the coating agent bonds to surfaces of the feed particles as the feed particles are milled; and
recirculating the milled aqueous slurry from the agitated media mill back to the disperser until the feed particles are milled to an average particle size of 100 nm or less.

29. The process of claim 28, wherein the coating agent includes a polymer or copolymer comprising acrylates or organosilicon compounds.

30. The process of claim 28, wherein the coating agent comprises ammonium polyacrylate.

31. The process of claim 28, wherein the dispersant comprises citric acid, a salt of citric acid, or a combination of citric acid and a salt of citric acid.

32. The process of claim 28, wherein the dispersant is present in the aqueous slurry in an amount in the range of from about 1% to about 20% by weight of water.

33. The process of claim 28, wherein the pH of the initial slurry is monitored and adjusted with aminomethyl propanol to maintain a basic pH of about 9.0 to 9.5.

34. The process of claim 28, wherein the agitated media mill uses milling media comprising zirconia beads having a particle size of 200 micron or less.

35. The process of claim 34, wherein the milling media comprises yttria stabilized zirconia beads having a particle size in the range of from about 50 micron to about 100 micron.

36. The process of claim 28, wherein the coating agent comprises at least one water soluble metal compound that binds to surfaces of the feed particles and to newly formed surfaces of the feed particles as a metal oxide, hydroxide or hydrous oxide to form a surface coating of the surface coated nanoparticles.

37. The process of claim 28, further comprising maintaining a temperature of the slurry in the disperser of 45° C. or below.

38. The process of claim 28, further comprising maintaining a temperature of the slurry in the disperser in a range of from about 45° C. to about 85° C.

39. The process of claim 28, wherein the dispersion of surface coated nanoparticles remains in a stable dispersed state for a period greater than two months.

40. A process for producing a stable aqueous dispersion of nanoparticles, the process comprising:

combining feed particles with a coating agent in a disperser to form a slurry having a solids content of about 35% or less by weight of slurry, wherein the feed particles comprise titanium dioxide having an anatase crystalline structure and an average primary particle size of 200 nm or greater;

circulating the slurry to an agitated media mill in closed loop with the disperser such that at least a portion of the coating agent bonds to surfaces of the feed particles as the feed particles are milled;

supplying an additional amount of feed particles to the slurry, the additional amount sufficient to increase the solids content of the slurry to a range of from about 35% to about 75% by weight of slurry; and circulating the slurry having a solids content in the range of from about 35% to about 75% by weight of slurry to the agitated media mill in closed loop with the disperser such that the coating agent bonds to surfaces of the feed particles as the feed particles are milled to an average particle size of 100 nm or less.

41. The process of claim 40, wherein the slurry having a solids content of about 35% or less by weight of slurry is milled to an average particle size of 100 nm or less prior to supplying the additional amount of feed particles.

42. The process of claim 40, wherein the coating agent comprises a polyacrylate polymer.

43. The process of claim 40, wherein the coating agent comprises an ammonium polyacrylate.

44. The process of claim 40, wherein the slurry is prepared using deionized water.

45. The process of claim 40, wherein the additional amount of feed particles is sufficient to increase the solids content of the slurry to a range of from about 45% to about 75% by weight of slurry.

46. The process of claim 40, wherein the slurry additionally contains a dispersant.

47. The process of claim 46, wherein the dispersant comprises citric acid, a salt of citric acid, or a combination of citric acid and a salt of citric acid.

48. The process of claim 40, wherein the dispersant is present in the aqueous slurry in an amount in the range of from about 1% to about 20% by weight of water.

49. The process of claim 40, wherein the pH of the initial slurry is monitored and adjusted with aminomethyl propanol to maintain a basic pH of about 9.0 to 9.5.

50. The process of claim 40, wherein the agitated media mill utilizes milling media comprising zirconia beads having a particle size of 200 micron or less.

51. The process of claim 50, wherein the milling media comprises zirconia beads having a particle size in the range of from about 50 micron to about 100 micron.

52. The process of claim 40, wherein the agitated media mill is filled to about 85 to 95 vol % with milling media.

53. The process of claim 40, wherein the coating agent comprises at least one water soluble metal compound that binds to surfaces of the feed particles and to newly formed surfaces of the feed particles as a metal oxide, hydroxide or hydrous oxide to from a surface coating of the surface coated nanoparticles.

54. The process of claim 40, wherein the dispersion of surface coated nanoparticles remains in a stable dispersed state for a period greater than two months.

* * * * *